US006488949B2

(12) United States Patent
Shafer et al.

(10) Patent No.: US 6,488,949 B2
(45) Date of Patent: *Dec. 3, 2002

(54) INHIBITING PHASE SEPARATION IN LOW VISCOSITY WATER-BASED PESTICIDE SUSPENSIONS

(75) Inventors: James G. Shafer, Gladstone, MO (US); Darrell C. Hudson, Liberty, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/071,539

(22) Filed: Feb. 8, 2002

(65) Prior Publication Data
US 2002/0110574 A1 Aug. 15, 2002

Related U.S. Application Data

(60) Division of application No. 09/759,797, filed on Jan. 12, 2001, now Pat. No. 6,379,687, which is a continuation-in-part of application No. 09/506,655, filed on Feb. 17, 2000, now abandoned, which is a continuation-in-part of application No. 09/228,904, filed on Jan. 11, 1999, now Pat. No. 6,074,987, which is a continuation-in-part of application No. 09/086,075, filed on May 28, 1998, now abandoned.

(51) Int. Cl.[7] .................... A01N 25/00; A01N 43/78; A61K 31/535; A61K 31/44; A61K 31/425
(52) U.S. Cl. .................... 424/405; 514/229.2; 514/342; 514/365
(58) Field of Search .................... 504/132; 424/405; 514/224.2, 342, 365

(56) References Cited

U.S. PATENT DOCUMENTS

| 3,060,084 A | | 10/1962 | Littler ...................... 167/42 |
| 3,737,551 A | | 6/1973 | Karsten et al. ............. 424/286 |
| 3,920,442 A | | 11/1975 | Albert et al. ................ 71/92 |
| 6,074,987 A | * | 6/2000 | Shafer et al. ............... 514/132 |

* cited by examiner

Primary Examiner—Alton Pryor
(74) Attorney, Agent, or Firm—Joseph C. Gil; Raymond J. Harmuth

(57) ABSTRACT

The present invention provides a composition for inhibiting phase separation and the resulting non-uniform distribution of an active ingredient in low viscosity, water-based pesticide suspensions. In accordance with this invention, the composition comprises from about 0.003% to about 50% by weight of a pesticide, from about 0.5% to about 10% by weight of a wetting agent; from about 0.0% to about 0.8% by weight of a thickener; from about 0.1% to about 0.5% of an antimicrobial agent; from about 5% to about 20% of an anti-freeze; from about 1% to about 8% of a hydrophobic fumed silica; and from about 40% to about 95% of water. In an embodiment of the invention, the hydrophobic fumed silica results from a hydrophilic silica which is treated with dimethyldichlorosilane.

5 Claims, No Drawings

INHIBITING PHASE SEPARATION IN LOW VISCOSITY WATER-BASED PESTICIDE SUSPENSIONS

This application is a divisional application of U.S. application Ser. No. 09/759,797, filed Jan. 12, 2001 now U.S. Pat. No. 6,379,687, which in turn is a continuation-in-part of U.S. application Ser. No. 09/506,655, filed Feb. 17, 2000 (now abandoned), which is a continuation-in-part of U.S. application Ser. No. 09/228,904, filed on Jan. 11, 1999 (now U.S. Pat. No. 6,074,987), which is a continuation-in-part of U.S. application Ser. No. 09/086,075, filed May 28, 1998 (now abandoned).

TECHNICAL FIELD OF THE INVENTION

The present invention relates to a composition for inhibiting phase separation and the resulting non-uniform distribution of an active ingredient in low viscosity, water-based pesticide suspensions. More particularly, the composition of the present invention comprises a hydrophobic fumed silica to inhibit phase separation and the resulting non-uniform distribution of an active ingredient in the low-viscosity, water-based pesticide suspension. The preferred hydrophobic fumed silica results from a hydrophilic silica which is treated with dimethyidichlorosilane.

BACKGROUND OF THE INVENTION

A pesticide suspension is a homogeneous mixture of small solid particles of pesticide suspended in a liquid medium. During periods of non-agitation, the solid particles with a density greater than the density of the liquid medium will settle toward the bottom of the container and homogeneity is not maintained. Similarly, solid particles with a density less than the density of the liquid medium will settle toward the top of the container and homogeneity is not maintained. The loss of homogeneity can cause product failure if it results in non-uniform applications of the pesticide, and plugging of strainers and nozzles used with application equipment. In practice, the usual ways to inhibit settling of the particles include (i) making the density of the liquid medium as close as possible to that of the solid pesticide, and/or (ii) building high viscosity into the suspension. Changing the density of the liquid medium is usually not feasible, and building high viscosity into the suspension causes problems in the production, handling and performance of the pesticide.

Therefore, the practice of combining or formulating the pesticide compounds with inert ingredients to facilitate their dispersibility in water, has developed. Such water dispersible formulations have generally been prepared by combining the pesticide with (i) an emulsifier or wetting agent, (ii) a dispersant, and (iii) an inert carrier or filler material. The inert carrier or filler material has been found necessary in order to obtain a suitable admixture of the emulsifier, dispersant and pesticide, and to facilitate the size reduction of these ingredients to an appropriate particle size. The inert carrier or filler material may be either a solid or a liquid. The former type of formulations include wettable powders such as those discussed in U.S. Pat. No. 3,737,551. Other types of solid formulations such as the water dispersible granules of U.S. Pat. No. 3,920,442, have been proposed. The latter type of formulations include flowables in which the major dispersing medium is water, such as those disclosed in U.S. Pat. No. 3,060,084.

The disadvantages of these formulations known in the art include difficulty in handling when preparing the suspensions, a tendency to cake during storage, and extreme sensitivity to high temperature. Thus, there has long been a need in the art for a flowable aqueous pesticide composition which is easily handled during preparation and use, which has excellent shelf-life even during extended storage and which is completely dispersible in water.

SUMMARY OF THE INVENTION

It is an object of the present invention to provide a composition for inhibiting phase separation and the resulting non-uniform distribution of an active ingredient in low viscosity, water-based pesticide suspensions. The composition contains from about 0.003% to about 50% by weight of a pesticide; from about 0.5% to about 10% by weight of a wetting agent; from about 0.0% to about 0.8% by weight of a thickener; from about 0.1% to about 0.5% of an antimicrobial agent; from about 5% to about 20% of an anti-freeze; from about 1% to about 8% of a hydrophobic fumed silica; and from about 40% to about 95% of water.

It is also an object of the present invention to provide a composition for inhibiting phase separation and the resulting non-uniform distribution of an active ingredient in low viscosity, water-based pesticide suspensions without changing the density of the liquid medium and/or building high viscosity into the suspension.

These and other objects that will be apparent to those skilled in the art are accomplished by adding hydrophobic fumed silica to the low-viscosity, water-based pesticide suspension. The preferred hydrophobic fumed silica results from a hydrophilic silica which is treated with dimethyidichlorosilane.

DETAILED DESCRIPTION OF THE PREFERRED EMBODIMENTS OF THE INVENTION

The composition of the present in ion.comprises a combination of a low viscosity water-based pesticide formulation .and hydrophobic fumed silica. In an embodiment of the present invention, "low viscosity" is defined as a viscosity of less than about 900 cps. The pesticide formulation includes a pesticides a wetting agent; a thickener; an antimicrobial agent; an antifreeze agent; and water.

In an embodiment of the present Invention, the pesticide demonstrates the following properties; a friable solid pesticide which is capable of being fractured or shattered into small particles, which has a melting point of less than about 60° C., and a water solubility of no more than about 1000 ppm at a temperature of about 40° C. Further, the pesticide is resistant to Ostwald ripening and its resulting crystal growth. Moreover, the pesticide is not easily hydrolyzed or degraded by an aqueous environment.

The pesticide of the present invention is selected from the group consisting of an insecticide, a fungicide, and a herbicide. Substantially any insecticide, fungicide or herbicide known in the art may be used. Preferred insecticides include the heterocyclic compounds described in U.S. Pat. Nos. 6,022,871; 5,852,012; 5,719,146; 5,034,404; 4,849,432; 4,742,060; and RE 35,811, the disclosures of which are herein incorporated by reference. In a particularly preferred embodiment of the invention, the insecticide is a chloronicotinyl or a chlorothiazole. Moreover, insecticides of the following general formulas (I), (II), (III) and (IV) are most preferred.

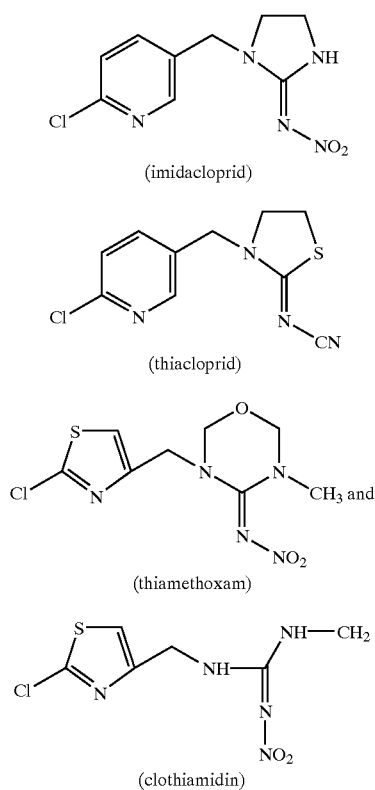

(imidacloprid) (I)

(thiacloprid) (II)

(thiamethoxam) (III)

(clothiamidin) (IV)

A preferred fungicide is tebuconazole, and a preferred herbicide is metribuzin.

Wetting agents serve to reduce the surface tension at the water-solid interface and therefore, increase the tendency of the water to contact the complete surface of the active ingredient particles. Both anionic and nonionic surfactants are useful. Examples of anionic surfactants include alkyl polyether alcohol sulfates, arylalkyl polyether alcohol sulfates, arylalkyl sulfonates, alkylnaphthalene sulfonates, and alkyl phenoxybenzene disulfonates. Nonionic surfactants include arylalkyl polyether alcohols, aklyl polyether alcohols, polyoxyethylene fatty acid esters, polyethylene sorbitan fatty acid esters, polyalkylene oxide block copolymers, polyalkylene oxide block copolymer monohydric alcohols and polyalkylene oxide block copolymer alkyl phenols. Preferred wetting agents include sodium naphthalene formaldehyde condensate and ethoxylated polyoxypropylene.

A thickener is generally a water soluble or water dispersible anionic colloid possessing shear thinning properties, low sensitivity to temperature, good stability in both acidic and basic media, and compatibility with most inorganic materials. Examples of thickening agents include polysaccharide gums such as xanthan gum, guar gum, gum arabic; organically modified montmorillonite clays, attapulgite clays, carboxy-vinyl copolymers, and cellulose ethers. Preferred thickeners include xanthan gum and hydroxypropyl methylcellulose.

An antimicrobial agent is generally used to prevent the growth of bacteria, fungi, or other microbial organisms that can flourish in an aqueous environment. Examples of antimicrobial agents include 1,2-benzisothiazolin-3-one, methyl or propyl parahydroxybenzoate, 2-bromo-2-nitro-propane-1,2-diol, sodium benzoate, glutaraldehyde, O-phenylphenol, 5-chloro-2-methyl-4-isothiazolin-3-one, pentachlorophenol, 2,4-dichlorobenzyl alcohol, and benzisothiazolinones. Preferred antimicrobial agents include 1,2-benzisothiazolin-3-one, 2-methyl-4-isothiazolin-3-one plus, 5-chloro-2-methyl-4-isothiazolin-3-one.

An anti-freeze agent (freeze point depressant) includes relatively low molecular weight aliphatic alcohols such as ethylene glycol, propylene glycol, glycerine, hexane diol, and sorbitol. Preferred anti-freeze agents include dipropylene glycol, glycerine, hexylene glycol, and propylene glycol.

Hydrophobic fumed silicas are made by treating the surface of hydrophilic fumed silicas with a substance that chemically bonds and, thereby, changes the surface from one that is easily wetted by water to one that adsorbs hardly any water (even at high levels of atmospheric moisture). The preferred hydrophobic fumed silica of the present invention comprises a hydrophilic fumed amorphous silica treated with dimethyidichlorosilane.

The composition of the pesticide suspension of the present invention is generally as follows.

|  | Weight % |
| --- | --- |
| Pesticide | 0.003–50 |
| Wetting Agent | 0.5–10 |
| Thickener | 0.0–0.8 |
| Antimicrobial Agent | 0.1–0.5 |
| Anti-Freeze | 5–20 |
| Hydrophobic Fumed Silica | 1–8 |
| Water | 40–95 |

The composition of the present invention contains from about 0.003% to about 50% by weight of a pesticide; from about 0.5% to about 10% by weight of a wetting agent; from about 0.0% to about 0.8% by weight of a thickener; from about 0.1% to about 0.5% of an antimicrobial agent; from about 5% to about 20% of an anti-freeze; from about 1% to about 8% of a hydrophobic fumed silica; and from about 40% to about 95% of water.

Having thus described our invention, the following examples are given as being illustrative thereof. All weights and percentages given are parts by weight or percentages by weight, unless otherwise indicated.

EXAMPLES

Example 1

A study was conducted to demonstrate the effectiveness of 0.5% to 7.0% hydrophobic amorphous fumed silica in reducing the settling rate of a water-based suspension concentrate (SC) containing 0.5 pound imidacloprid insecticide per gallon.

[A.] SC Concentrate with 0% Hydrophobic Fumed Silica

Blended together and homogenized by means of a Ross high-shear mixer were 152 grams of sodium naphthalene formaldehyde condensate (wetting agent), 152 grams of ethoxylated polyoxypropylene (wetting agent), 38 grams of a 19% solution of 1,2-benzisothiazolin-3-one in aqueous dipropylene glycol (antimicrobial agent), 14 grams of xanthan gum (thickener), 759 grams of glycerine (anti-freeze) and 4856 grams of deionized water. A suspension containing 0.5 pound imidacloprid insecticide per gallon was prepared by blending 5962 grams of this mixture with 2139 grams ADMIRE 2, a water-based suspension concentrate containing 2 pounds imidacloprid insecticide per gallon manufactured by Bayer Corporation, and mixed to uniformity with a low-shear paddle mixer. The final make-up of the suspension was then 5.6% imidacloprid insecticide, 2.4% sodium naphthalene formaldehyde condensate, 2.4% ethoxylated polyoxypropylene, 0.5% 1,2-benzisothiazolin-3-one solution, 0.2% xanthan gum, 12.0% glycerine, and 76.9% water.

[B.] SC Concentrate with 0.5% Hydrophobic Fumed Silica

The composition as described in [A.] was used with the following noted exceptions, (i) 4815 grams of deionized water were used in the composition, (ii) 40 grams of hydrophobic fumed silica resulting from dimethyldichlorosilane treated hydrophilic fumed silica were added to the composition and homogeneously dispersed with the Ross high-shear mixer, and (iii) the final make-up of the suspension contained 76.4% water, and 0.5% hydrophobic silica.

[C.] SC Concentrate with 1.0% Hydrophobic Fumed Silica

The composition as described in [B.] was used with the following noted exceptions, (i) 4775 grams of deionized water were used, (ii) 81 grams of hydrophobic fumed silica resulting from dimethyldichlorosilane treated hydrophilic fumed silica were added, and (iii) the final make-up of the suspension contained 75.9% water, and 1.0% hydrophobic silica.

[D.] SC Concentrate with 4.0% Hydrophobic Fumed Silica

The composition as described in [C.] was used with the following noted exceptions, (i) 4532 grams of deionized water were used, (ii) 324 grams of hydrophobic fumed silica resulting from dimethyldichlorosilane treated hydrophilic fumed silica were added, and (iii) the final make-up of the suspension contained 72.9% water, and 4.0% hydrophobic silica.

[E.] SC Concentrate with 6.0% Hydrophobic Fumed Silica

The composition as described in [D.] was used with the following noted exceptions, (i) 4369 grams of deionized water were used, (ii) 486 grams of hydrophobic fumed silica resulting from dimethyidichlorosilane treated hydrophilic fumed silica were added, and (iii) the final make-up of the suspension contained 70.9% water, and 6.0% hydrophobic silica.

[F.] SC Concentrate with 7.0% Hydrophobic Fumed Silica

The composition as described in [E.] was used with the following noted exceptions, (i) 4289 grams of deionized water were used, (ii) 567 grams of hydrophobic fumed silica resulting from dimethyidichlorosilane treated hydrophilic fumed silica were added, and (iii) the final make-up of the suspension contained 69.9% water, and 7.0% hydrophobic silica.

Each of these six suspensions was then stored at 50° C. for 56 days in a 1-quart clear glass jar with a lid. Storage at 50° C. increases the rate of chemical decomposition and physical degradation as opposed to storage at room temperature or below. After 3 days of storage, the settling of solid insecticide particles in the suspension with 0% hydrophobic silica resulted in the top 40% of the suspension being a clear liquid (syneresis); storage for 21 days resulted in settling that left the top 70% of the suspension a clear liquid. The addition of 0.5% to 7.0% hydrophobic amorphous fumed silica significantly reduced the settling rates. The results are shown in Table 1.

TABLE 1

WATER-BASED SUSPENSION CONTAINING 0.5 POUND IMIDACLOPRID INSECTICIDE PER GALLON AND 0.5% TO 7.0% HYDROPHOBIC FUMED SILICA

| Hydrophobic Amorphous Silica, % | Viscosity* cps 20° C. | Syneresis, % | | | |
|---|---|---|---|---|---|
| | | 3 days 50° C. | 21 days 50° C. | 28 days 50° C. | 56 days 50° C. |
| 0 | 200 | 40 | 70 | — | — |
| 0.5 | 200 | 5 | 20 | — | — |
| 1.0 | 200 | 5 | 10 | 34 | 59 |
| 4.0 | 250 | 6 | 6 | 6 | 12 |
| 6.0 | 260 | <1 | 2 | — | — |
| 7.0 | 350 | <1 | 1 | — | — |

*spdl #3 @ 60 rpm.

Example 2

A study was conducted to compare the effectiveness of 0.5% hydrophobic amorphous silica with that of 0.5% hydrophilic silica in reducing the settling rate of suspensions containing 0.5 pound per gallon of (i) imidacloprid insecticide, (ii) metribuzin herbicide, or (iii) tebuconazole fungicide.

[A.] Imidacloprid Suspension with 0.5% Hydrophobic Fumed Silica

Blended together and homogenized by means of a Ross high-shear mixer, were 56 grams of Morwet D425 (sodium naphthalene formaldehyde condensate; wetting agent), 56 grams Witconol 324 (ethoxylated polyoxypropylene; wetting agent), 14 grams Proxel GXL (a 19% solution of 1,2-benzisothiazolin-3-one in aqueous dipropylene glycol; antimicrobial agent), 5 grams Rhodopol 50 MD (xanthan gum; thickener), 280 grams glycerine (anti-freeze), and 1789 grams deionized water. Then 15 grams of Aerosil R-972 (hydrophobic fumed silica resulting from dimethyidichlorosilane treated hydrophilic fumed silica) was added and homogeneously dispersed with the Ross high-shear mixer. A suspension containing 0.5 pound imidacloprid per gallon was prepared by blending 294 grams of this mixture with 106 grams ADMIRE 2, and mixed to uniformity with a low-shear paddle mixer. The final concentration of imidacloprid in the suspension was 5.6%; the concentration of hydrophobic silica was 0.5%.

[B.] Imidacloprid Suspension with 0.5% Hydrophilic Fumed Silica

The composition as described in [A.] was used with the following exception, 15 grams of Aerosil 200 (hydrophilic fumed silica) were added to the [B.] mixture instead of the Aerosil R-972 (hydrophobic fumed silica) which was added to the [A.] mixture.

[C.] Metribuzin Suspension with 0.5% Hydrophobic Fumed Silica

The composition as described in [A.] was used with the following exception, a metribuzin suspension, instead of an imidacloprid suspension was used. In [C.], a suspension containing 0.5 pound metribuzin per gallon was prepared by blending 368 grams of this mixture with 32 grams SENCOR 70 WP, a wettable powder containing 70% metribuzin herbicide manufactured by Bayer Corporation, and mixed to uniformity with a low-shear paddle mixer. The final concentration of metribuzin in the suspension was 5.6%; the concentration of hydrophobic silica was 0.5%.

[D.] Metribuzin Suspension with 0.5% Hydrophilic Fumed Silica

The composition as described in [C.] was used with the following exception, 15 grams of Aerosil 200 (hydrophilic fumed silica) were added to the [D.] mixture instead of the Aerosil R-972 (hydrophobic fumed silica) which was added to the [C.] mixture.

[E.] Tebuconazole Suspension with 0.5% Hydrophobic Fumed Silica

The composition as described in [A.] was used with the following exception, a tebuconazole suspension, instead of an imidacloprid suspension was used. In [E.], a suspension containing 0.5 pound tebuconazole per gallon was prepared by blending 342 grams of this mixture with 58 grams FOLICUR 3.6, a water-based suspension concentrate containing 3.6 pounds tebuconazole fungicide per gallon manufactured by Bayer Corporation, and mixed to uniformity with a low-shear paddle mixer. The final concentration of tebuconazole in the suspension was 5.6%; the concentration of hydrophobic silica was 0.5%.

[F.] Tebuconazole Suspension with 0.5% Hydrophilic Fumed Silica

The composition as described in [E.] was used with the following exception, 15 grams of Aerosil 200 (hydrophilic fumed silica) were added to the [F.] mixture instead of the Aerosil R-972 (hydrophobic fumed silica) which was added to the [E.] mixture.

Each of these six suspensions was stored at 50° C. for 21 days in a 1-quart clear glass jar with a lid. The results of these storage tests are shown in Tables 2, 3, and 4.

Table 2 indicates that during the 21 day storage period, the hydrophobic silica, Aerosil R-972, was significantly more effective in reducing syneresis in the metribuzin and tebuconazole suspensions than the hydrophilic silica, Aerosil 200, or no silica. The syneresis reduction in the imidacloprid suspension was similarly significant for 10 days storage. However, the similarities of the effectiveness of 0.5% hydrophobic silica, 0.5% hydrophilic silica, and 0% silica at 14 and 21 days was attributed to this particular imidacloprid suspension needing more than 0.5% silica to show significant differences. For confirmation purposes, a follow-up study was conducted and the results are shown in Table 5.

Table 3 shows that the use of the hydrophobic silica achieved reduced syneresis without resulting in high viscosities either before or after storage.

Table 4 shows the use of hydrophobic silica achieved reduced syneresis without resulting in sediment that was difficult to disperse following storage.

Table 5 shows the results of storage of PREMISE 0.5 SC (Imidicloprid) suspensions containing 0.5%–1.0% hydrophilic silica (Aerosil 200) and 0.5% to 4.0% hydrophobic silica (Aerosil R-972). All suspensions were made using the materials and processes used to make the PREMISE 0.5 SC for the study reported in Table 2. The data shows that at concentrations of 0.5% silica or greater, the hydrophobic silica is significantly more effective in reducing syneresis than the hydrophilic silica.

TABLE 2

| | % SYNERESIS AFTER STORAGE AT 50° C. | | | | | | | | |
|---|---|---|---|---|---|---|---|---|---|
| | SENCOR 0.5 SC (METRIBUZIN) | | | FOLICUR 0.5 SC (TEBUCONAZOLE) | | | PREMISE 0.5 SC (IMIDACLOPRID) | | |
| TEST | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil |
| 3 days | 3 | 28 | 46 | 11 | 21 | 37 | 5 | 20 | 40 |
| 10 days | 5 | 51 | 59 | 20 | 60 | 66 | 20 | 40 | 50 |
| 14 days | 10 | 68 | 69 | 31 | 61 | 84 | 50 | 60 | 60 |
| 21 days | 14 | 69 | 69 | 41 | 64 | 87 | 52 | no data | 66 |

TABLE 3

| | VISCOSITY AFTER STORAGE AT 50° C. | | | | | | | | |
|---|---|---|---|---|---|---|---|---|---|
| | SENCOR 0.5 SC (METRIBUZIN) | | | FOLICUR 0.5 SC (TEBUCONAZOLE) | | | PREMISE 0.5 SC (IMIDACLOPRID) | | |
| TEST | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil |
| 0 days | 170 | 188 | 164 | 152 | 182 | 152 | 200 | 235 | 200 |
| 21 days | 224 | 194 | 174 | 174 | 176 | 170 | 210 | no data | 208 |

TABLE 4

SEDIMENTATION and REDISPERSION AFTER STORAGE FOR 21 DAYS AT 50° C.

| TEST | SENCOR 0.5 SC (METRIBUZIN) | | | FOLICUR 0.5 SC (TEBUCONAZOLE) | | | PREMISE 0.5 SC (IMIDACLOPRID) | | |
|---|---|---|---|---|---|---|---|---|---|
| | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil | 0.5% Aerosil R972 (Hydrophobic) | 0.5% Aerosil 200 (Hydrophilic) | 0.0% Aerosil |
| Sedimentation | none | slight sediment | slight sediment | none | none | slight sediment | none | no data | none |
| Ease of Redispersion | very easy | easy w/ agitation | *easy w/ agitation | very easy | easy w/ agitation | difficult ** | very easy | no data | easy |

*Very slight residue on bottom that was somewhat difficult to redisperse.
**Some sediment/residue on the bottom was difficult to redisperse, requiring a lot of shaking.

TABLE 5

PREMISE 0.5 SC WITH 0.5% TO 4.0% SILICA

| Spl ID | Additive Name | Wt % | TESTS | 3 days @ 50° C. | 10 days @ 50° C. | 14 days @ 50° C. | 21 days @ 50° C. |
|---|---|---|---|---|---|---|---|
| A | None | 0.0 | Viscosity | 200 | — | — | — |
| | | | Syneresis | 30–40% | 50% | 60% | 66% |
| | | | Redispersion | easy | easy | easy | easy |
| | | | Demarcation | sharp | sharp | sharp | sharp |
| | | | Sediment | none | no tacky sediment | no tacky sediment | no tacky sediment |
| B | Aerosil 200 Hydrophilic | 0.5 | Viscosity | 224 | 200 | — | — |
| | | | Syneresis | 20% | 40% | >60% | |
| | | | Redispersion | very easy | very easy | No further evaluations performed | — |
| | | | Demarcation | fuzzy/flock | sharp | | |
| | | | Sediment | none | none | | |
| C | Aerosil R972 Hydrophobic | 0.5 | Viscosity | 200 | 210 | 210 | — |
| | | | Syneresis | 5% | 5% | 10% | 20% |
| | | | Redispersion | very easy | very easy | very easy | very easy |
| | | | Demarcation | indistinct w/agglomerate | sharp | sharp | sharp |
| | | | Sediment | none | none | no tacky sediment | none |
| D | Aerosil 200 Hydrophilic | 0.75 | Viscosity | 296 | — | — | — |
| | | | Syneresis | 10% | >50% | | |
| | | | Redispersion | very easy | No further evaluations performed | — | — |
| | | | Demarcation | fuzzy | | | |
| | | | Sediment | none | | | |
| E | Aerosil R972 Hydrophobic | 0.75 | Viscosity | 201 | 220 | 210 | — |
| | | | Syneresis | 5% | 5% | 10% | 15% |
| | | | Redispersion | very easy | very easy | very easy | very easy |
| | | | Demarcation | indistinct w/agglomerate | slight flock | sharp w/slight flock | sharp |
| | | | Sediment | none | no tacky sediment | no tacky sediment | none |
| F | Aerosil 200 Hydrophilic | 1.0 | Viscosity | 350 | — | — | — |
| | | | Syneresis | 10% | >50% | | |
| | | | Redispersion | very easy | No further evaluations performed | — | — |
| | | | Demarcation | fuzzy | | | |
| | | | Sediment | none | | | |
| G | Aerosil R972 Hydrophobic | 1.0 | Viscosity | 201 | 205 | — | — |
| | | | Syneresis | 5% | 5% | 5% | 10% |
| | | | Redispersion | very easy | very easy | very easy | very easy |
| | | | Demarcation | indistinct w/agglomerate | medium flock | light flock | sharp |
| | | | Sediment | none | no tacky sediment | no tacky sediment | none |
| H | Aerosil R972 Hydrophobic | 2.0 | Viscosity | 200 | — | — | — |
| | | | Syneresis | 5% | 6% | | |
| | | | Redispersion | easy | very easy | — | — |
| | | | Demarcation | sharp | sharp | | |
| | | | Sediment | none | none | | |
| I | Aerosil R972 Hydrophobic | 3.0 | Viscosity | 230 | — | — | — |
| | | | Syneresis | 2% | | | |
| | | | Redispersion | easy | very easy | — | — |
| | | | Demarcation | sharp | sharp | | |
| | | | Sediment | none | none | | |

TABLE 5-continued

PREMISE 0.5 SC WITH 0.5% TO 4.0% SILICA

| Spl ID | Additive Name | Wt % | TESTS | 3 days @ 50° C. | 10 days @ 50° C. | 14 days @ 50° C. | 21 days @ 50° C. |
|---|---|---|---|---|---|---|---|
| J | Aerosil R972 Hydrophobic | 4.0 | Viscosity Syneresis Redispersion Demarcation Sediment | 254 trace very easy n/a none | — 1% very easy sharp none | — | — |

What is claimed is:

1. A low viscosity water-based pesticide suspension having inhibited phase separation and inhibited non-uniform distribution of an active ingredient within said water-based pesticide suspension, said active ingredient being a pesticide selected from the group consisting of an insecticide, a fungicide and a herbicide, said pesticide suspension comprising:
   a. from about 0.003% to about 50% by weight of said pesticide, wherein said pesticide is a friable solid which is capable of being fractured or shattered into small particles, said pesticide having a melting point of less than about 60° C. and a water solubility of no more than about 1000 ppm at about 40° C., which said pesticide is resistant to Ostwalds ripening and crystal growth and is resistant to hydrolysis or degradation in an aqueous environment;
   b. from about 0.5% to about 10% by weight of a wetting agent selected from the group consisting of sodium naphthalene formaldehyde condensate and ethoxylated polyoxypropylene;
   c. from 0.0% to about 0.8% by weight of a thickener selected from the group consisting of xanthan gum and hydroxypropyl methylcellulose;
   d. from about 0.1% to about 0.5% by weight of an antimicrobial agent selected from the group consisting of 1,2-benzisothiazolin-3-one, 2-methyl-4-isothiazolin-3-one and, 5-chloro-2-methyl-4-isothiazolin-3-one;
   e. from about 5% to about 20% by weight of an anti-freeze agent selected from the group consisting of dipropylene glycol, glycerine, hexylene glycol, and propylene glycol;
   f. from about 1% to about 8% by weight of an hydrophobic silica wherein said hydrophobic silica is a hydrophilic fumed silica treated with dimethyldichlorosilane; and
   g. from about 40% to about 95% by weight of water,
wherein said pesticide suspension has a viscosity of less than about 900 cps.

2. The pesticide suspension of claim 1 wherein, when said pesticide is said insecticide, said insecticide is selected from the group consisting of chloronicotinyls and chlorothiazoles, when said pesticide is said fungicide, said fungicide is tebuconazole, and when said pesticide is said herbicide, said herbicide is metribuzin.

3. The pesticide suspension of claim 2 wherein said pesticide is said insecticide and wherein said insecticide is selected from the group consisting of imidacloprid, thiacloprid, thiamethoxam and clothiamidin.

4. A low viscosity water-based pesticide suspension having inhibited phase separation and inhibited non-uniform distribution of an active ingredient within said water-based pesticide suspension, said active ingredient being a pesticide selected from the group consisting of an insecticide, a fungicide and a herbicide, said pesticide suspension comprising:
   a. from about 0.003% to about 50% by weight of said pesticide, wherein when said pesticide is said insecticide, said insecticide is selected from the group consisting of chloronicotinyls and chlorothiazoles, when said pesticide is said fungicide, said fungicide is tebuconazole, and when said pesticide is said herbicide, said herbicide is metribuzin;
   b. from about 0.5% to about 10% by weight of a wetting agent selected from the group consisting of sodium naphthalene formaldehyde condensate and ethoxylated polyoxypropylene;
   c. from 0.0% to about 0.8% by weight of a thickener selected from the group consisting of xanthan gum and hydroxypropyl methylcellulose;
   d. from about 0.1% to about 0.5% by weight of an antimicrobial agent selected from the group consisting of 1,2-benzisothiazolin-3-one, 2-methyl-4-isothiazolin-3-one and, 5-chloro-2-methyl4-isothiazolin-3-one;
   e. from about 5% to about 20% by weight of an anti-freeze agent selected from the group consisting of dipropylene glycol, glycerine, hexylene glycol, and propylene glycol;
   f. from about 1% to about 8% by weight of an hydrophobic silica wherein said hydrophobic silica is a hydrophilic fumed silica treated with dimethyidichlorosilane; and
   g. from about 40% to about 95% by weight of water,
wherein said pesticide suspension has a viscosity of less than about 900 cps.

5. The pesticide suspension of claim 4 wherein said pesticide is said insecticide and wherein said insecticide is selected from the group consisting of imidacloprid, thiacloprid, thiamethoxam and clothiamidin.

\* \* \* \* \*